United States Patent [19]

Carmosin et al.

[11] Patent Number: 5,332,736
[45] Date of Patent: Jul. 26, 1994

[54] ANTI-CONVULSANT AROYL AMINOACYLPYRROLES

[75] Inventors: Richard J. Carmosin, Quakertown; John R. Carson, Norristown; Philip M. Pitis, North Wales, all of Pa.

[73] Assignee: Ortho Pharmaceutical Corporation, Raritan, N.J.

[21] Appl. No.: 149,094

[22] Filed: Nov. 1, 1993

[51] Int. Cl.$^5$ ............... A61K 31/40; A61K 31/535; C07D 207/30; C07D 413/06

[52] U.S. Cl. .............. 514/235.5; 514/212; 514/326; 514/397; 514/422; 514/423; 540/602; 544/141; 546/208; 548/314.7; 548/518; 548/539

[58] Field of Search ............ 540/602; 544/141; 546/208; 548/518, 539, 314.7; 514/212, 235.5, 326, 397, 422, 423

[56] References Cited

FOREIGN PATENT DOCUMENTS 102561 8/1980 Japan.

*Primary Examiner*—Robert W. Ramsuer

[57] ABSTRACT

Aroyl aminoacyl pyrroles are pharmaceutically useful as anti-convulsants, which includes utility for the treatment of epilepsy.

11 Claims, No Drawings

5,332,736

ANTI-CONVULSANT AROYL AMINOACYLPYRROLES

This invention relates to anti-convulsants, particularly those contemplated for use in the treatment of epilepsy. Stated otherwise, this invention relates to aroyl aminoacyl pyrroles which are useful as anti-convulsants.

BACKGROUND OF THE INVENTION

The conditions grouped under the term epilepsy constitute an area of continuing medical need. Coatsworth estimated that available medication controlled seizures in only 50% of patients and decreased the incidence in only 75% of patients (NINDS Monograph No. 12, HEW Publication No.(NIH) 73-51, 1971 U.S. Government Printing Office, Washington D.C.). Since the time of his estimate, a handful of new drugs have entered clinical practice worldwide. The impact of these newly emerging drugs has yet to be fully evaluated.

The currently used anti-epileptic drugs such as phenytoin and carbamazepine contain a urea function as well as aryl rings. They prevent

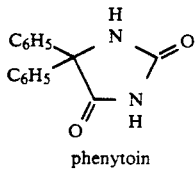
phenytoin

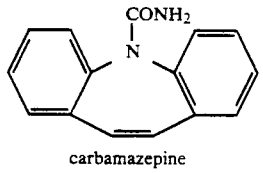
carbamazepine

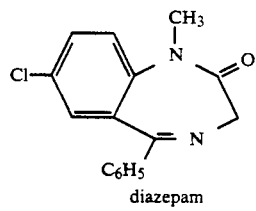
diazepam seizure spread and are useful in treating generalized tonic-clonic and complex partial seizures. Sodium valproate is a simple branched chain aliphatic carboxylate salt. It elevates seizure threshold as well as prevents seizure spread. The benzodiazepines (diazepam, clonazepam, nitrazepam, clobazam) elevate seizure threshold and are used to treat generalized absence seizures.

Among the newly emerging drugs, several structural classes are apparent. Oxcarbamazepine is closely related to carbamazepine. Vigabatrin, gabapentin

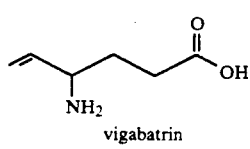
vigabatrin

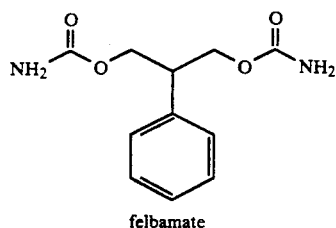
felbamate

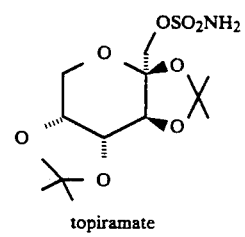
topiramate and progabide, though they may not be mechanistically homogeneous, all share the GABA backbone. Topiramate and zonisamide both have a sulfamyl group. Felbamate is a biscarbamate. Of all the structural classes of anticonvulsants, the only drug to show the pattern of two aromatic rings and a dialkylaminoalkyl chain, which is so prevalent among CNS drugs, is flunarizine.

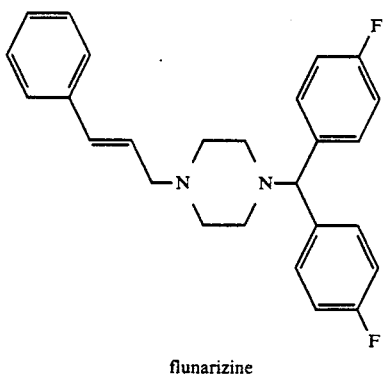
flunarizine

The structures of newer anticonvulsants have been summarized (Drugs of the Future 1991, 16: 317-320).

No theories have been put forward which would explain why many epileptic patients are currently not adequately treated with current therapy. The strategy of seeking drugs which are structurally, mechanistically and pharmacologically unique seems to be the most appropriate approach to improving current therapy. We describe herein a series of anticonvulsant aroyl aminoacyl pyrroles which, we believe, fulfill these criteria.

SUMMARY OF THE INVENTION

Briefly, there are provided by the present invention compounds having anti-convulsant activity of the formula:

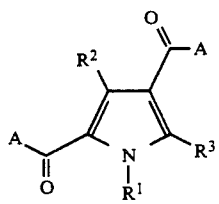

(I)

wherein,

A is simultaneously both

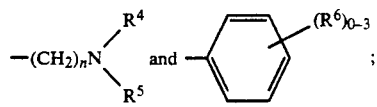

n is an integer from 1 to 5;

$R^1$ is selected from the group consisting of H and $C_{1-4}$alkyl;

$R^2$ and $R^3$ are selected from the group consisting of H and $C_{1-4}$alkyl;

$R^4$ and $R^5$ are independently selected from the group consisting of H, $C_{1-4}$alkyl, phenyl $C_{1-4}$alkyl and substituted phenyl $C_{1-4}$alkyl where the substituent is on phenyl and selected from the group consisting of methyl and methoxy, or in the alternative, are fused and together with said nitrogen form a heterocyclic ring selected from the group consisting of:

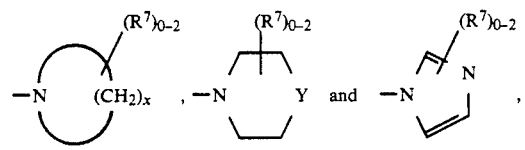

wherein Y is S or O, x is 3 to 7 and $R^7$ is selected from the group consisting of methyl and hydroxymethyl; and $R^6$ is selected from the group consisting of halo, $C_{1-4}$alkyl, $C_{1-4}$alkoxy, hydroxy, nitro, amino, $C_{1-4}$acylamino, cyano, trihalo$C_{1-4}$alkyl, $C_{1-4}$alkylsulfonyl, $C_{1-4}$alkylsulfinyl, and $C_{1-4}$acyl, including pharmaceutically acceptable acid additon salts thereof.

DETAILED DESCRIPTION OF THE INVENTION

The compounds of the present invention may be placed into two categories, those having benzoyl at the 2-position and those having benzoyl at the 4-position. Both categories of compounds may be prepared by variations of what is fundamentally the same reaction scheme.

Scheme 1 exemplifies the preparation of compounds having benzoyl at the 2-position. Referring to Scheme 1, in the first step a simple pyrrole A1 is acylated with an appropriately substituted benzoyl chloride B1 to produce benzoyl pyrrole C1. This acylation may be carried out by simply heating the benzoyl chloride and the pyrrole in an aprotic solvent followed by removing excess benzoyl chloride by reaction with a dibasic amine and extraction with HCl. Typical of the aprotic solvents which may be utilized are aromatic hydrocarbons, such as, benzene, toluene, xylene, chlorobenzene, nitrobenzene, etc.; paraffins, such as, methyl cyclohexane, octane, etc.; halocarbons, such as, methylene chloride, chloroform, tetrachloroethane, etc.; ethers, such as, diethyl ether, diglyme, etc.; ketones, such as, methyl ethyl ketone, cyclohexanone, etc.; esters, such as, ethyl butyrate, etc.; nitroalkanes, such as, nitropropane, etc.; or carbon disulfide. The temperature of the acylation will vary depending upon the desired rate of reaction and the substituents of pyrrole A1. Preferably the acylation is carried out at a temperature of from 50° to 250° C. A suitable dibasic amine is dimethyl-3-aminopropyl amine. In the case where $R^1$ is hydrogen the acylation, as described, may not produce desirable yields. In this case, a Vilsmeier type acylation as employed by J. White and G. McGillivrey, J. Org. Chem., Vol. 42, pp 42–48, 1977 might be expeditiously employed. Subsequently, benzoyl pyrrole C1 is acylated at the 4-position in a Friedel-Crafts reaction with acid chloride D1 to produce 2-benzoyl-4-alkanoyl pyrrole E1. The Friedel-Crafts reaction is carried out by causing the carboxylic acid chloride D1, in which X is Cl, Br or I, to react with product C1 in a solvent with a Friedel-Crafts reagent followed by treatment with HCl and evaporation of the solvent. Suitable Friedel-Crafts reagents include aluminum chloride, zinc chloride, $BF_3$ or $TiCl_4$. Suitable solvents include methylene chloride, 1,2-dichloroethane, carbon tetrachloride or chloroform. The reaction temperature might vary between −20° and 150° C. In the case where $R^6$ is amine, it will not survive the Friedel-Crafts reaction in good yield. Thus, it should be protected with well known protecting groups or present as a suitable precursor substituent, such as, nitro which can thereafter be converted to amine. In the third reaction, 2-benzoyl-4-alkanoyl pyrrole E1 is aminated with amine F1 to produce the desired 2-benzoyl-4-aminoalkanoyl pyrrole G1. The amination may be carried out by heating the reactants E1 and F1 neat or in a solvent to a temperature of from 40° to 120° C. and preferably from 50° to 90° C. Suitable solvents, where employed, include ethanol, i-propanol or toluene.

SCHEME 1

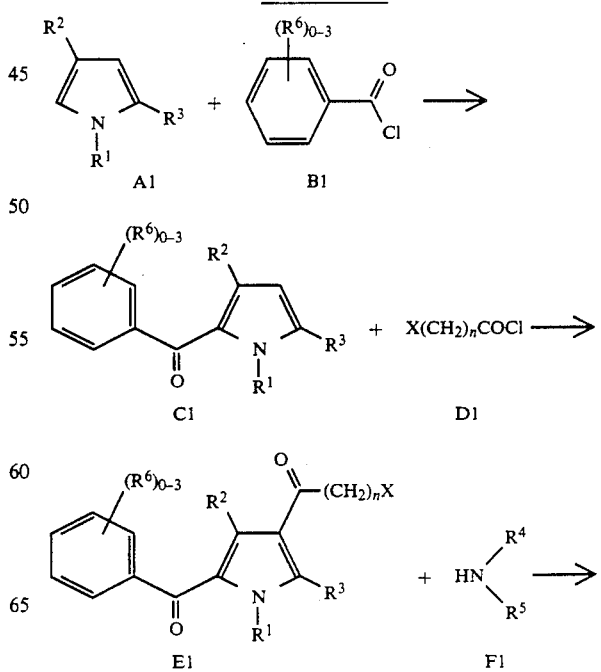

-continued
SCHEME 1

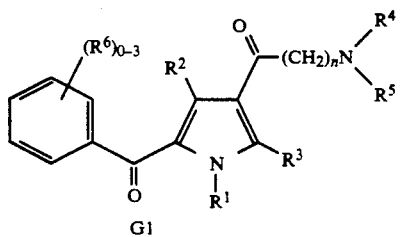

G1

Scheme 2 exemplifies the preparation of compounds having benzoyl at the 4-position. Except for the specifics of the reactants, each step of Scheme 2 is analogous to the corresponding step of Scheme 1 with the reactions and description thereof being identical. Referring to Scheme 2, in the first step a simple pyrrole A2 is acylated with an appropriately substituted alkanoyl chloride B2 to produce alkanoyl pyrrole C2. Subsequently, alkanoyl pyrrole C2 is acylated at the 4-position in a Friedel-Crafts reaction with benzoic acid chloride D2 to produce 2-alkanoyl-4-benzoyl pyrrole E2. In the third reaction, 2-alkanoyl-4-benzoyl pyrrole E2 is aminated with amine F2 to produce the desired 2-aminoalkanoyl-4-benzoyl pyrrole G2.

SCHEME 2

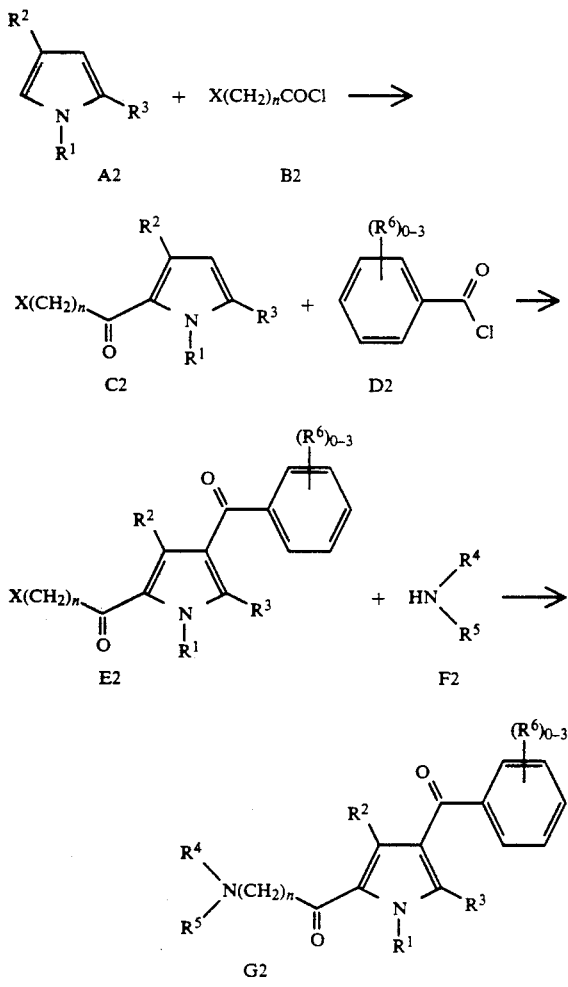

Preferred $R^1$ include hydrogen, methyl, ethyl, n-propyl and i-propyl. In the most preferred compounds, $R^1$ is methyl.

Preferred $R^2$ and $R^3$ include hydrogen, methyl, ethyl, n-propyl and i-propyl. In the most preferred compounds, $R^2$ and $R^3$ are hydrogen and methyl.

Preferred $R^4$ and $R^5$, where independently selected, include hydrogen, methyl, ethyl, n-propyl, i-propyl, benzyl and phenylethyl where the phenyl ring may be mono- or di-substituted with a substituent selected from the group of methyl and methoxy. In the most preferred compounds, $R^4$ and $R^5$, where independently selected, are hydrogen, methyl and in at most one instance benzyl.

Preferred $R^4$ and $R^5$, where fused and depicted together with nitrogen, include:

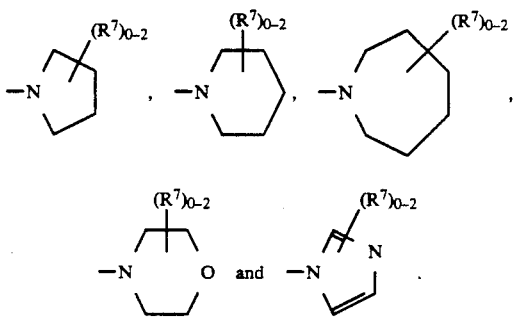

In the most preferred compounds, $R^4$ and $R^5$, where fused and depicted together with nitrogen, are piperidin-1-yl, pyrrolidin-1-yl, morpholin-1-yl and imidazol-1-yl.

Preferred $R^6$ include bromine, chlorine, methyl, ethyl, methoxy, ethoxy, hydroxy, nitro, amino, formylamino, acetylamino, cyano, perfluoromethyl, 3,3,3-trifluoropropyl, methylsulfonyl, methylsulfinyl, formyl, and acetyl. In the most preferred compounds, $R^6$ is non-existant, methyl or chloro.

The compounds herein readily form pharmacertically acceptable acid addition salts. Such salts include hydrochlorides, sulfates, phosphates, methane sulfonates, fumarates, maleates, citrates, lactates, and the like. Those skilled in the art will readily recognize suitable methods for manufacture and use of the acid addition salts.

The compound of formula (I) are useful as anticonvulsant agents. The anticonvulsant activity of the subject compounds was determine using a standard "maximal electroshock test" (MES). In this test, activity is indicated by a block of the toxic extensor seizure, as described by Swinyard et al in J. Pharmacol,. Exptl. Therap. 106, 319 (1952). A more recent description of current anticonvulsant drug screening is given in Swinyard et al., in Epilepsia 19, 409 (1978).

The anticonvulsant activity of compounds of this invention tested according to the Swinyard (1952) method is shown in the following Table I:

TABLE 1

| Example Compound | Mouse MES test, $ED_{50}$ (mg/kg, i.p.) |
|---|---|
| 9-1 | 24.36 |
| 9-2 | 87.61 |
| 9-3 | 23.86 |
| 9-3 | 8.97 |
| 9-4 | 14.40 |

TABLE 1-continued

| Example Compound | Mouse MES test, ED$_{50}$ (mg/kg, i.p.) |
| --- | --- |
| 9-5 | 15.19 |
| 9-10 | 5.38 |
| 9-11 | 27.53 |
| 9-14 | 159.2 |
| 9-24 | 16.46 |
| 9-25 | 37.44 |
| 9-27 | 86.23 |
| 9-29 | 33.01 |
| 9-30 | 49.14 |
| 9-32 | 10.33 |
| 9-34 | 14.94 |

For treating epilepsy, a compound of formula (I) may be employed at a daily dosage in the range of about 30 to 2000 mg, usually in 2 to 4 divided doses, for an average adult human. A unit dose would contain about 10 to 500 mg of the active ingredient.

In general, compounds of formula (I) may be used in treating epilepsy in a manner similar to that used for phenytoin. Medical aspects of the treatment of epilepsy are described in L. S. Goodman et al in "The Pharmacological Basis of Therapeutics", 5th Ed. pages 201 to 226, Macmillan (1975).

To prepare the pharmaceutical compositions of this invention, one or more compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carder. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit, e.g., tablet, capsule, powder, injection, teaspoonful, suppository and the like, from about 10 to about 500 mg of the active ingredient.

The foregoing compositions are particularly suitable for use in the treatment of epilepsy or the symptoms of epilepsy by a method comprising internally administering to a subject suffering from the symptoms of epilepsy compositions comprising an effective epilepsy inhibiting amount of a compound of formula (I).

The following examples are offered by way of illustration and not by way of limitation.

EXAMPLE 1

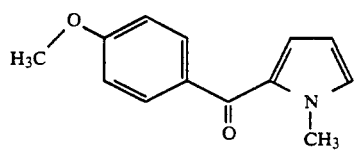

(4-Methoxyphenyl)(1-methyl-1H-pyrrol-2-yl)-methanone

A solution of 5 g (0.06 mole) N-methylpyrrole and 13.3 g (0.078 mole) of 4-methoxybenzoyl chloride in 50 mL of dry toluene was heated under reflux overnight with an argon stream bubbling through the reaction mixture. After cooling, 40 mL of 20% 3-dimethylaminopropylamine in H$_2$O was added and the mixture stirred for 45 minutes. Diethyl ether was added and the organic solution was washed with 1N HCl, NaHCO$_3$, water, brine and dried (MgSO$_4$). The solvent was evaporated in vacuo and the residue recrystallized from ethanol to give 3.68 g of product: mp. 66°-68° C.; mass spectrum (CH$_4$—Cl) m/z=216 (M+1); NMR (CDCl$_3$) d 7.85 (d, 2H); 6.9-7.1 (d,s, 3H); 6.7 (d, 1H); 6.15 (d, 1H); 4.1 (s, 3H); 3.9 (s, 3H). Anal Calcd for C$_{13}$H$_{13}$NO$_2$: C, 72.54; H, 6.09; N, 6.51. Found: C, 72.59; H, 6.06; N, 6.43.

EXAMPLE 2

By the procedure of example 1, employing the appropriate aroyl chloride in place of 4-methoxybenzoylchloride, the following products were produced: (2-chlorophenyl)(1-methyl-1H-pyrrol-2-yl)-methanone: mp 55°-57° C. (1-methyl-1H-pyrrol-2-yl)(4-nitrophenyl)-methanone: mp 148°-150° C. (3-chlorophenyl)(1-methyl-1H-pyrrol-2-yl)-methanone: bp 115°-116° C. (0.004 Torr)

EXAMPLE 3

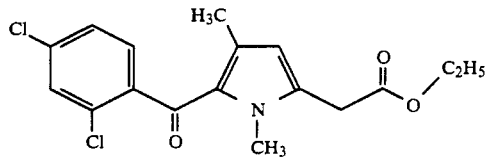

Ethyl 5-(2,4-dichlorobenzoyl)-1,4-dimethyl-1H-pyrrole-2-acetate (3)

A solution of 50 g (0.276 mole) of ethyl 1,4-dimethyl-1H-pyrrole-2-acetate and 64 g (0.303 mole) of 2,4-dichlorobenzoyl chloride in 310 mL of xylene was heated under reflux for 4 h under argon. After cooling, a 20% solution of 3-dimethylaminopropylamine in H$_2$O was added and stirred one hour. The organic layer was washed twice with 1N HCl, water, brine, and dried (MgSO$_4$). Evaporation of the solvent in vacuo gave a solid which was recrystallized from methanol to give 79.39 g of product: mp 90°-92° C.; mass spectrum (Cl—CH$_4$) m/z=354 (M+1); NMR 300 MHz (CDCl$_3$) d 7.5 (s, 1H); 7.3 (dd, 2H); 6.0 (s, 1H); 4.2 (q, 2H); 3.9 (s, 3H); 3.65 (s, 2H); 1.6 (s, 3H); 1.25 (t, 3H). Anal Calcd for C$_{17}$H$_{17}$Cl$_2$NO$_3$: C, 57.64; H, 4.84; N, 3.95. Found: C, 57.52; H, 4.60; N, 3.80.

EXAMPLE 4

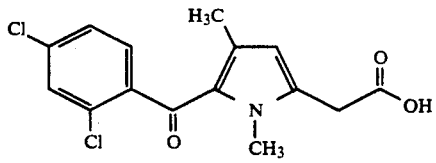

5-(2,4-Dichlorobenzoyl)-1,4-dimethyl-1H-pyrrole-2-acetic acid (4)

A solution of 2.38 mL (1.1 eq) of 1N NaOH was added dropwise to a refluxing solution of 76.89 g (0.217 mole) of ethyl 5-(2,4-dichlorobenzoyl)-1,4-dimethyl-1H-pyrrole-2-acetat (3)in 750 mL absolute ethanol. The mixture was heated under reflux for 20 minutes. The reaction was poured into 3N HCl/ice and extracted three times with diethyl ether. The organics were washed with water (twice), brine, and dried (MgSO$_4$). Evaporation of the solvent in vacuo gave a tan oil which was crystallized from acetonitrile to give 63.05 g of product: mp 140°-143° C.; mass spectrum (Cl—CH$_4$) m/z=326 (M+1); NMR 300 MHz (Me$_2$SO-d$_6$) d 7.8 (s, 1H); 7.6 (m, 1H); 7.4 (m, 1H); 6.0 (s, 1H); 3.8 (s, 3H); 3.75 (s, 2H); 1.45 (s, 3H). Anal Calcd for C$_{15}$H$_{13}$Cl$_2$NO$_3$: C, 55.24; H, 4.02; N, 4.29. Found: C, 55.47; H, 3.84; N, 4.29.

EXAMPLE 5

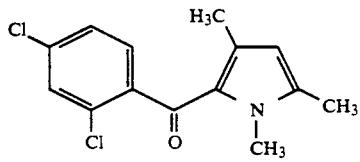

(2,4-Dichlorophenyl)(1,3,5-trimethyl-1H-pyrrol-2-yl)-methanone (5)

A solution of 62.69 g (0.18 mole) 5-(2,4-dichlorobenzoyl)-1,4-dimethyl-1H-pyrrole-2-acetic acid (4)in 550 mL of propionic acid was heated under reflux overnight then poured into water. The solution was extracted three times with diethyl ether. The ether solution was washed successively with NaHCO$_3$, water and brine, and dried (MgSO$_4$). Evaporation of the solvent in vacuo gave a tan solid which was recrystallized from methylcyclohexane: mp 96°-98° C.; mass spectrum (Cl—CH$_4$) m/z=282 (M+1); NMR 300 MHz (CDCl$_3$) d 7.5 (s, 1H); 7.35-7.2 (m, 2H); 5.8 (s, 1H ); 3.9 (s, 3H); 2.25 (s, 3H); 1.6 (s, 3H). Anal Calcd for C$_{14}$H$_{13}$Cl$_2$NO: C, 59.59; H, 4.64; N, 4.96. Found: C, 59.79; H, 4.39; N, 4.92.

EXAMPLE 6

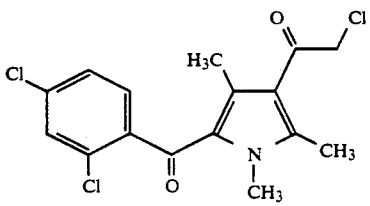

2-Chloro-1-[5-(2,4-Dichlorobenzoyl)-1,2,4-trimethyl-1H-pyrrol-3-yl]-ethanone (6)

A solution of 48.65 g (0.17 mole) of (2,4-dichlorophenyl)(1,3,5-trimethyl-1H-pyrrol-2-yl)-methanone (5) in 480 mL 1,2-dichloroethane was cooled in an ice bath and 53.5 g (0.425 mole) of AlCl$_3$ was added in four portions. A 33.5 mL portion of (0.425 mole) chloroacetyl chloride was added dropwise. The ice bath was removed and the reaction allowed to stir for 3 h under argon. A 10 g sample of AlCl$_3$ was added and the reaction was stirred overnight. The mixture was poured into 1N HCl/ice and the organic layer was separated. The aqueous layer was extracted twice with methylene chloride. The organics were combined and washed with water, NaHCO$_3$, water, brine, and dried (MgSO$_4$). The solvent was evaporated in vacuo and the residue recrystallized from methylcyclohexane to give 53.50 g of product: mp 100°-102° C.; mass spectrum (Cl—CH$_4$) m/z=358 (M+1); NMR 300 MHz (CDCl$_3$) d 7.55 (s, 1H); 7.4 (s, 2H); 4.4 (s, 2H); 3.7 (s, 3H); 2.5 (s, 3H); 1.9 (s, 3H). Anal Calcd for C$_{16}$H$_{14}$NO$_2$: C, 53.58; H, 3.93; N, 3.91. Found: C, 53.48; H, 3.81; N, 3.93.

EXAMPLE 7

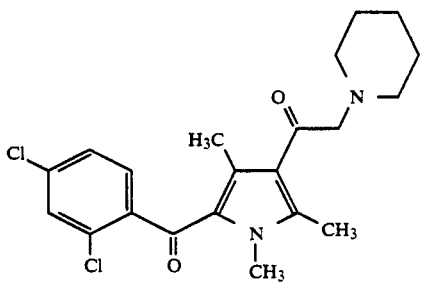

1-[5-(2,4-Dichlorobenzoyl)-1,2,4-trimethyl-1H-pyrrol-3-yl]-2-(1-piperidinyl)-ethanon (7)

A solution of 8.0 g (0.022 mole) of 2-chloro-1-[5-(2,4-dichlorobenzoyl)-1,2,4-trimethyl-1H-pyrrol-3-yl]-ethanone (6) and 4.64 mL (0.066 mole) of piperidine in 130 mL of 2-propanol was heated under reflux for 1.5 h. The reaction was cooled and the solvent evaporated in vacuo. The residue was partitioned between diethyl ether and water and the organic solution was extracted twice with 1N HCl. A solid was removed by filtration and the filtrate was made basic with sodium bicarbonate. The mixture was extracted with diethyl ether and the ether solution was washed with water, brine and dried (MgSO$_4$). The solvent was evaporated in vacuo. The product was converted to the hydrochloride salt and recrystallized from 2-propanol to give 5.97 g of product: mp 177°-179° C.; mass spectrum (Cl—CH$_4$) m/z=393 (m+1); NMR 300 MHz (Me$_2$SO-d$_6$) d 7.85 (s, 1H); 7.6-7.5 (m, 2H); 4.7 (s, 2H); 3.8 (s, 3H); 3.6-3.4 (m, 2H); 3.2-3.0 (m, 2H); 2.6 (s, 3H); 2.0 (br s, 4H) 1.8 (s 3H). Anal Calcd for C$_{20}$H$_{22}$Cl$_2$N$_2$O$_2$: C, 55.22; H, 5.87; N, 6.05. Found: C, 55.06; H, 5.89; N, 6.05.

EXAMPLE 8

Using the procedure of Example 6 and employing the appropriate aryl pyrrolyl methanone in place of (2,4-dichlorphenyl)(1,3,5-trimethyl-1H-pyrrol-2-yl)-methanone and the appropriate Ψ-chloroacyl choride in place of chloroacetyl chloride, there were obtained the following products (8-1 through 8-9):

| No. | Ar | $R^1$ | $R^2$ | $R^3$ | n |
|---|---|---|---|---|---|
| 8-1 | p-ClPh | $CH_3$ | H | H | 1 |
| 8-2 | p-ClPh | $CH_3$ | $CH_3$ | $CH_3$ | 1 |
| 8-3 | o-ClPh | $CH_3$ | H | H | 1 |
| 8-4 | p-$CH_3$OPh | $CH_3$ | H | H | 1 |
| 8-5 | p-$NO_2$Ph | $CH_3$ | H | H | 1 |
| 8-6 | m-ClPh | $CH_3$ | H | H | 1 |
| 8-7 | p-ClPh | H | H | H | 1 |
| 8-8 | p-ClPh | $CH_3$ | H | H | 3 |
| 8-9 | p-Cl | $CH_3$ | $CH_3$ | $CH_3$ | 4 |

They are described as follows:

| No. | M.P. °C. | Yield % | Formula | Calc'd/ Found |
|---|---|---|---|---|
| 8-1 | 163 | 68.1 | $C_{14}H_{11}Cl_2NO_2$ | C,56.78; H,3.74; N,4.73 C,56.63; N,8.82; N,4.63 |
| 8-2 | 141–143 | 31 | $C_{16}H_{15}Cl_2NO_2$ | C,59.28; H,4.66; N,4.32 C,59.32; H,4.73; N,4.33 |
| 8-3 | 121–124 | 91 | $C_{14}H_{11}Cl_2NO_2$ | C,56.78; H,3.74; N,4.73 C,56.72; H,3.66; N,4.70 |
| 8-4 | 157–159 | 90 | $C_{15}H_{14}ClNO_2$ | C,61.76; H,4.84; N,4.80 C,61.51; H,4.70; N,4.69 |
| 8-5 | 173–176 | 60 | $C_{14}H_{11}ClN_2O_4$ | C,54.83; H,3.61; N,9.1 C,55.11; H,3.70; N,9.10 |
| 8-6 | 116–119 | 67 | $C_{14}H_{11}Cl_2NO_2$ | C,56.78; H,3.74; N,4.73 C,56.87; H,3.83; N,4.77 |
| 8-7 | 196–197 | 91 | $C_{13}H_9Cl_2NO_2$ | C,55.35; H,3.22; N,4.96 C,55.76; H,2.84; N,4.86 |
| 8-8 | 95–97 | 39 | $C_{16}H_{15}Cl_2NO_2$ | C,59.28; H,4.66; N,4.32 C,59.44; H,4.24; N4.24 |
| 8-9 | 60–65 | 79 | $C_{19}H_{21}Cl_2NO_2$ | C,62.30; H,5.78; N,3.82 C,62.35; H,5.74; N,3.75 |

EXAMPLE 9

Using the procedure of Example 7 and employing the appropriate 1-(5-aroylpyrrol-3-yl)-y-chloroalkanone in place of 2-chloro-1-[5-(2,4-dichlorobenzoyl)-1,2,4-trimethyl-1H-pyrrol-3-yl]-ethanone and the appropriate amine in place of piperidine, there were obtained the following products (9-1 through 9-38):

| No. | n | $R^1$ | $R^2/R^3$ | $R^4/R^5$ | Ar |
|---|---|---|---|---|---|
| 9-1 | 1 | $CH_3$ | H/H |  | p-ClPh |
| 9-2 | 1 | $CH_3$ | $CH_3$/$CH_3$ |  | p-ClPh |
| 9-3 | 1 | $CH_3$ | $CH_3$/$CH_3$ | | p-ClPh |
| 9-4 | 1 | $CH_3$ | H/H | $CH_2CH_3$/ $CH_2CH_3$ | p-ClPh |
| 9-5 | 1 | $CH_3$ | $CH_3$/$CH_3$ | | p-ClPh |
| 9-6 | 1 | $CH_3$ | $CH_3$/$CH_3$ |  | p-ClPh |

-continued

[Structure: pyrrole with Ar-C(=O)- at 5-position, R² at 4-position, -C(=O)-(CH₂)ₙ-NR⁴R⁵ at 3-position, R³ at 2-position, R¹ on N]

| No. | n | R¹ | R²/R³ | R⁴/R⁵ | Ar |
|---|---|---|---|---|---|
| 9-7 | 1 | CH₃ | CH₃/CH₃ | H / -CH₂CH₂-(3,4-dimethoxyphenyl) | p-ClPh |
| 9-8 | 1 | CH₃ | H/H | tetrahydropyranyl | p-ClPh |
| 9-9 | 1 | CH₃ | CH₃/CH₃ | CH₃ / benzyl(-CH₂CH₂-Ph) | p-ClPh |
| 9-10 | 1 | CH₃ | H/H | cyclohexyl | o-ClPh |
| 9-11 | 1 | CH₃ | H/H | cycloheptyl | p-ClPh |
| 9-12 | 1 | CH₃ | H/H | cyclopentyl | o-ClPh |
| 9-13 | 1 | CH₃ | H/H | 2,6-dimethyltetrahydropyran-4-yl | p-ClPh |
| 9-14 | 1 | CH₃ | H/H | 1-Adamantyl | o-ClPh |
| 9-15 | 1 | CH₃ | H/H | (hydroxymethyl)cyclohexyl | p-ClPh |
| 9-16 | 1 | CH₃ | H/H | cyclooctyl | p-ClPh |
| 9-17 | 1 | CH₃ | H/H | pyrrol-2-yl (with N) | p-CH₃OPh |

-continued

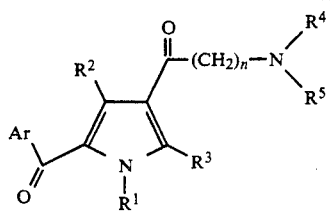

| No. | n | R¹ | R²/R³ | R⁴/R⁵ | Ar |
|---|---|---|---|---|---|
| 9-18 | 1 | CH₃ | H/H | cyclohexyl | p-CH₃OPh |
| 9-19 | 1 | CH₃ | H/H | tetrahydropyranyl (O) | o-ClPh |
| 9-20 | 1 | CH₃ | H/H | tetrahydropyranyl (O) | p-NO₂Ph |
| 9-21 | 1 | CH₃ | H/H | cyclohexyl | p-NO₂Ph |
| 9-22 | 1 | CH₃ | H/H | 4,4-dimethylcyclohexyl | p-ClPh |
| 9-23 | 1 | CH₃ | H/H | cyclohexyl | m-ClPh |
| 9-24 | 1 | CH₃ | H/H | cyclopentyl | m-ClPh |
| 9-25 | 1 | CH₃ | H/H | tetrahydropyranyl (O) | m-ClPh |
| 9-26 | 1 | H | H/H | cyclopentyl | p-ClPh |
| 9-27 | 1 | H | H/H | tetrahydropyranyl (O) | p-ClPh |
| 9-28 | 1 | CH₃ | H/H | H/CH₂CH₃ | p-ClPh |
| 9-29 | 1 | CH₃ | H/H | CH₂CH₃/CH₂CH₃ | p-CH₃OPh |
| 9-30 | 1 | CH₃ | H/H | cyclopentyl | p-ClPh |

-continued

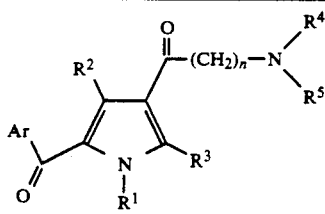

| No. | n | R¹ | R²/R³ | R⁴/R⁵ | Ar |
|---|---|---|---|---|---|
| 9-31 | 1 | $CH_3$ | H/H | ⌐ (pyrrolidine) | p-ClPh |
| 9-32 | 1 | $CH_3$ | $CH_3$/$CH_3$ | $CH_2CH_3$/$CH_2CH_3$ | p-ClPh |
| 9-33 | 1 | $CH_3$ | H/H | (cyclopentyl ring) | p-$CH_3$OPh |
| 9-34 | 1 | $CH_3$ | $CH_3$/$CH_3$ | $CH_2CH_3$/$CH_2CH_3$ | 2,4-diClPh |
| 9-35 | 1 | $CH_3$ | $CH_3$/$CH_3$ | $CH_3$/$CH_3$ | 2,4-diClPh |
| 9-36 | 1 | $CH_3$ | H/H | $CH_3$, imidazolyl | p-ClPh |
| 9-37 | 4 | $CH_3$ | $CH_3$/$CH_3$ | $CH_2CH_3$/$CH_2CH_3$ | p-ClPh |
| 9-38 | 4 | $CH_3$ | $CH_3$/$CH_3$ | (cyclohexyl ring) | p-ClPh |

They are described as follows:

| No. | M.P. °C. | Formula | calc'd found | rxn solv |
|---|---|---|---|---|
| 9-1 | 114–116 | $C_{19}H_{21}ClN_2O_2$ | 66.18, 6.14, 8.12 / 66.45, 6.12, 7.9 | neat |
| 9-2 | 96–98 | $C_{20}H_{23}ClN_2O_3$ | 64.08, 6.18, 7.47 / 64.14, 6.16, 7.38 | i-PrOH |
| 9-3 | 102–104 | $C_{21}H_{25}ClN_2O_2$ | 61.62, 6.40, 6.84 / 61.58, 6.67, 6.64 | EtOH |
| 9-4 | 182–185 | $C_{18}H_{21}ClN_2O_2$—HCl | 58.54, 6.01, 7.51 / 58.57, 6.00, 7.66 | EtOH |
| 9-5 | 115–117 | $C_{20}H_{23}ClN_2O_2$ | 66.94, 6.46, 7.81 / 67.10, 6.40, 7.76 | i-PrOH |
| 9-6 | 195–197 | $C_{19}H_{18}ClN_3O_2$ | 64.14, 5.10, 11.81 / 64.02, 4.99, 11.75 | i-PrOH |
| 9-7 | 210–213 | $C_{26}H_{29}ClN_2O_4$—HCl | 61.78, 5.98, 5.54 / 61.70, 5.92, 5.48 | i-PrOH |
| 9-8 | 131–135 | $C_{18}H_{19}ClN_2O_3$ | 62.41, 5.53, 8.09 / 62.44, 5.91, 8.05 | i-PrOH |
| 9-9 | 155–156 | $C_{24}H_{25}ClN_2O_2$—$C_2H_2O_4$** | 62.59, 5.45, 5.54 / 62.56, 5.62, 5.61 | i-PrOH |
| 9-10 | 169–171 | $C_{19}H_{21}ClN_2O_2$—$C_4H_4O_4$* | 59.94, 5.47, 6.08 / 59.68, 5.40, 5.98 | i-PrOH |
| 9-11 | 195–198 | $C_{20}H_{23}ClN_2O_2$—HCl·0.25 $H_2O$ | 60.08, 6.18, 7.01, $H_2O$1.13 / 60.02, 6.16, 7.01, $H_2O$1.29 | i-PrOH |
| 9-12 | 113–116 | $C_{18}H_{19}ClN_2O_2$—HCl | 58.87, 5.49, 7.63 / 59.02, 5.53, 7.58 | i-PrOH |
| 9-13 | 258–260 | $C_{20}H_{23}ClN_2O_3$—HCl | 58.40, 5.88, 6.81 / 58.17, 5.85, 6.76 | i-PrOH |
| 9-14 | 248(d) | $C_{24}H_{27}N_2O_2$—HCl·0.25$H_2O$ | 63.79, 6.36, 6.20 $H_2O$0.25 / 63.79, 6.36, 6.20 $H_2O$0.25 | i-PrOH |
| 9-15 | 87–88 | $C_{19}H_{21}ClN_2O_3$—0.8$C_4H_4O_4$-2/3 $H_2O$* | 57.93, 5.28, 5.87 / 57.46, 5.54, 5.83 | i-PrOH |
| 9-16 | 211–213 | $C_{21}H_{25}ClN_2O_2$—HCl·0.25$H_2O$ | 60.95, 6.45, 6.77 / 61.13, 6.51, 6.90 | i-PrOH |
| 9-17 | 136–138 | $C_{18}H_{17}N_3O_3$ | 66.86, 5.30, 13.00 / 66.90, 5.31, 12.87 | i-PrOH |
| 9-18 | 190–192 | $C_{20}H_{24}N_2O_3$—HCl | 63.74, 6.69, 7.43 / 63.55, 6.66, 7.34 | i-PrOH |
| 9-19 | 125–127 | $C_{18}H_{19}ClN_2O_3$ | 62.34, 5.52, 8.08 / 62.57, 5.49, 8.04 | i-PrOH |
| 9-20 | 141–143 | $C_{18}H_{19}N_3O_5$ | 60.50, 5.36, 11.76 / 60.59, 5.24, 11.67 | i-PrOH |
| 9-21 | 225–227 | $C_{19}H_{21}N_3O_4$—HCl | 58.24, 5.66, 10.72 / 58.20, 5.79, 10.52 | i-PrOH |
| 9-22 | 105–107 | $C_{21}H_{25}ClN_2O_2$ | 67.64, 6.76, 7.51 / 67.67, 6.74, 7.58 | i-PrOH |
| 9-23 | 190–193 | $C_{19}H_{21}ClN_2O_2$—HCl | 59.85, 5.82, 7.35 / 59.92, 5.85, 7.41 | i-PrOH |
| 9-24 | 243–245 | $C_{18}H_{19}ClN_2O_2$—$HClO_4$ | 50.13, 4.67, 6.50 / 50.21, 4.65, 6.50 | neat |
| 9-25 | 198–200 | $C_{18}H_{19}ClN_2O_2$—HCl | 56.41, 5.26, 7.31 / 56.49, 5.24, 7.30 | i-PrOH |
| 9-26 | 242–245 | $C_{17}H_{17}ClN_2O_2$—$HClO_4$ | 48.94, 4.35, 6.71 / 49.01, 4.38, 6.72 | i-PrOH |
| 9-27 | 173–176 | $C_{17}H_{17}ClN_2O_3$ | 61.35, 5.10, 8.42 / 61.21, 5.13, 8.59 | i-PrOH |
| 9-28 | 259–262 | $C_{16}H_{17}ClN_2O_2$— | 55.58, 5.39, 8.10 | i-PrOH |

-continued

| No. | M.P. °C. | Formula | calc'd found | rxn solv |
|---|---|---|---|---|
| 9-29 | 165–168 | $C_{19}H_{24}N_2O_3$ HCl | 55.93, 5.56, 8.07 62.55, 6.91, 7.68 62.25, 6.93, 7.60 | i-PrOH |
| 9-30 | 118–122 | $C_{18}H_{19}ClN_2O_2$ | 65.35, 5.79, 8.47 65.29, 5.85 | neat |
| 9-31 | 173–175 | $C_{17}H_{17}ClN_2O_2$— $C_2H_2O_4$ | 56.10, 4.71, 6.89 55.71, 4.68, 6.82 | i-PrOH |
| 9-32 | 176–178 | $C_{20}H_{25}ClN_2O_2$ $1.5C_4H_4O_4$ 0.1EtOH* | 58.31, 5.91, 5.18 57.96, 5.85, 5.18 | i-PrOH |
| 9-33 | 114–115 | $C_{19}H_{22}N_2O_3$— HCl-0.6H$_2$O— | 61.07, 6.53, 7.50 60.74, 6.83, 7.29 | i-PrOH |
| 9-34 | 165–168 | $C_{20}H_{24}Cl_2O_2$— $C_4H_4O_4$* | 56.37, 5.52, 5.48 56.34, 5.70, 5.43 | i-PrOH |
| 9-35 | 119 | $C_{18}H_{20}Cl_2O_2$ HCl-0.75H$_2$O | 51.75, 5.48, 6.55, H$_2$O3.71 51.77, 5.44, 6.71, H$_2$O3.31 | toluene |
| 9-36 | 218–219 | $C_{18}H_{16}ClN_2N_3O_2$ | 63.25, 4.72, 12.29 63.20, 4.82, 12.27 | i-PrOH |
| 9-37 | 71–73 | $C_{23}H_{31}ClN_2O_2$ | 68.56, 7.75, 6.95 68.52, 7.86, 6.90 | neat |
| 9-38 | 177–178 | $C_{24}H_{31}ClN_2O_2$— $C_4H_4O_4$* | 63.33, 6.64, 5.28 63.25, 6.67, 5.23 | i-PrOH |

*fumarate salt
**oxalate salt

EXAMPLE 10

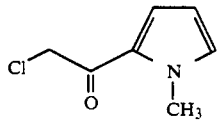

2-Chloro-1-(1-Methyl-1H-pyrrol-2-yl)-ethanone (10)

A solution of 15 g (0.186 mole) N-methylpyrrole and 19.2 mL (0.186 mole) chloroacetyl chloride in 600 mL dry THF was heated under reflux overnight with a nitrogen stream bubbling through the reaction mixture. After cooling, the organics were washed with water, 1N NaOH, water, brine and dried (MgSO$_4$). Evaporation of the solvent gave 31.2 g of a green solid: mp (decomp.) 280° C.; NMR 300 MHz (CDCl$_3$) d 7.05 (d, 1H); 6.95 (s, 1H); 6.2 (m, 1H); 4.5 (s, 2H); 3.9 (s, 3H).

EXAMPLE 11

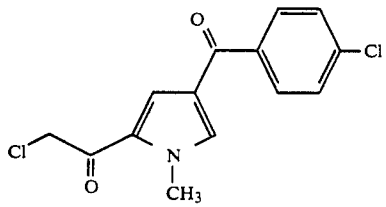

2-Chloro-1-[4-(4-chlorobenzoyl)-1-methyl-1H-pyrrol-2-yl]-ethanone (11)

A solution of 30 g (0.19 mole) of 2-chloro-1-(1-methyl-1H-pyrrol-2-yl)-ethanone (10) in 180 mL 1,2-dichloroethane (DCE) under an argon atmosphere was cooled in an ice bath and 60 g AlCl$_3$ (0.45 mole) was added in portions. After stirring for 10 minutes, a solution of 24 mL (0.19 mole) 4-chlorobenzoyl chloride in 110 mL DCE was added dropwise. The ice bath was removed and the reaction was stirred at room temperature overnight. The reaction was poured into 1N HCl/ice and the aqueous layer was extracted three times with methylene chloride. The organics solutions were combined, washed with water, 1N NaOH, water, brine, and dried (MgSO$_4$). Evaporation of the solvent in vacuo gave a solid which was recrystallized from ethyl acetate/methylcyclohexane to give 27.67 g of a solid: mp 130°–132° C.; NMR 300 MHz (CDCl$_3$) d 7.8 (m, 2H); 7.6–7.4 (m, 4H); 4.5 (s, 2H); 4.0 (s, 3H). Anal Calcd for $C_{14}H_{11}Cl_2NO_2$: C, 56.78; H, 3.74; N, 4.73. Found: C, 56.72; H, 3.76; N, 4.73.

EXAMPLE 12

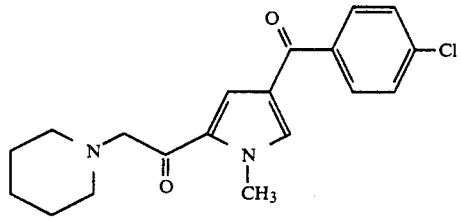

1-[4-(4-Chlorobenzoyl)-1-methyl-1H-pyrrol-2-yl]-2-(1-piperidinyl)-ethanone (12)

A solution of 4 g (0.013 mole) of 2-chloro-1-[4-(4-chlorobenzoyl)-1-methyl-1H-pyrrol-2-yl]-ethanone (11) and 4.08 mL (0.039 mole) of piperidine in 60 mL 2-PrOH was heated under reflux for 1 h. The solvent was evaporated in vacuo and the residue was taken up in diethyl ether/THF, washed with water, brine, and dried (MgSO$_4$). Evaporation of the solvent gave a tan solid which was recrystallized from 2-PrOH to give 3.65 g of product: mp 129°–130° C.; mass spectrum (Cl—CH$_4$) m/z=345 (M+1); NMR 300 MHz (CDCl$_3$) d 7.8 (m, 2H); 7.6 (s, 1H); 7.45 (d, 2H); 7.35 (s, 1H); 4.0 (s, 3H); 3.6 (s, 2H); 2.5 (br s, 4H); 1.6 (m, 4H); 1.4 (m, 2H). Anal Calcd for $C_{19}H_{21}Cl_2N_2O_2$: C, 66.18; H, 6.14; N, 8.12. Found: C, 66.25; H, 6.16; N, 8.08.

EXAMPLE 13

By the procedure of example 12 and employing the appropriate amine in place of piperidine the following products were prepared:

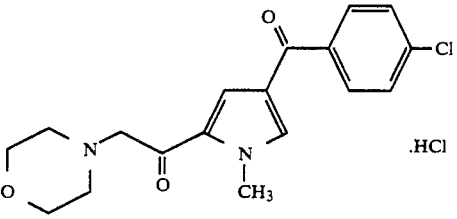

1-[4-(4-Chlorobenzoyl)-1-methyl-1H-pyrrol-2-yl]-2-(1-morpholino)-ethanone hydrochloride (13-1): mp 264°–267° C. Anal Calcd for $C_{18}H_{19}ClN_2O_3$·HCl: C, 56.41; H, 5.26; N, 7.31. Found: C, 56.14; H, 5.50; N, 7.17.

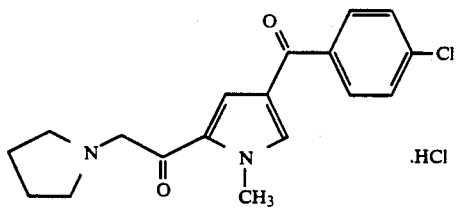

1-[4-(4-Chlorobenzoyl)-1-methyl-1H-pyrrol-2-yl]-2-(1-pyrrolidinyl)-ethanone hydrochloride (13-2): mp 265°-267° C. Anal Calcd for C$_{18}$H$_{19}$ClN$_2$O$_2$.HCl: C, 58.87; H, 5.49; N, 7.63. Found: C, 58.83; H, 5.66; N, 7.54.

EXAMPLE 14

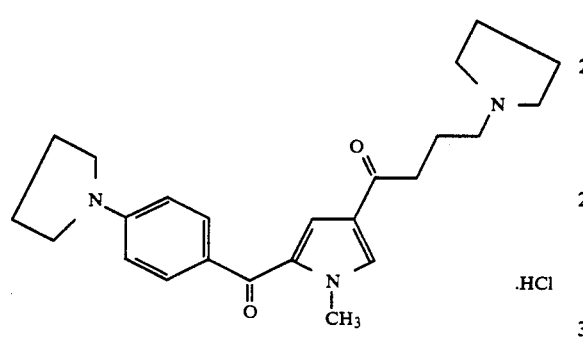

4-(Pyrrolidin-1-yl)-1-[5-(4-pyrrolidin-1-ylbenzoyl)-1-methyl-1H-pyrrol-3-yl]-butanone hydrochloride (14)

A 10 g (0.03 mole) sample of 4-chloro-1-[5-(4-chlorobenzoyl)-1-methyl-1H-pyrrol-3-yl]-butanone was added to 18 mL (0.216 mole) of pyrrolidine and the mixture heated under reflux for 4 h. The solvent was evaporated in vacuo and the residue triturated with Et$_2$O. The mixture was filtered and the filtrate treated with ethereal HCl to give the salt. Recrystallization from CH$_3$CN gave 1.18 g (9% yield) of a yellow solid: mp 203°-206° C. $^1$H NMR (Me$_2$SO-d$_6$) d 1.85-2.05 (m, 10H); 2.87-3.05 (m, 4H); 3.1-3.15 (m, 2H); 3.3-3.4 (m, 4H); 3.45-3.55 (broad s, 2H); 3.9 (s, 3H); 6.62 (d, 2H); 6.96 (s, 1H); 7.72 (d, 2H); 7.92 (s, 1H). Anal Calcd for C$_{24}$H$_{31}$N$_3$O$_2$. HCl. 0.4CH$_3$CN: C, 66.73; H, 7.50; N,10.67. Found: C,66.34; H,7.43; N, 10,33.

EXAMPLE 15

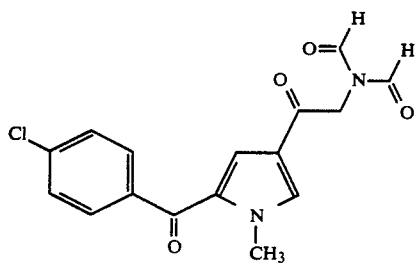

2-[(Bis-formyl)amino]-1-[5-(4-chlorobenzoyl)-1-methyl-1H-pyrrol-3-yl]-ethanone (15)

A solution of 10 g (0.034 mole) of 2-chloro-1-[5-(4-chlorobenzoyl)-1-methyl-1H-pyrrol-3-yl]-ethanone and 3.8 g (0.041 mole) sodium diformylamide in 80 mL acetonitrile was heated under reflux overnight under argon. An additional 2.0 g portion of sodium diformylamide was added and reflux was continued for 1.5 hrs. After evaporation of the solvent in vacuo the residue was passed through a flash column (silica gel, 3:1 hexane:acetone the 2:1 hexane:acetone) to give 6.18 g of a solid. mp 279°-282° C. 260° C. decomp. mass spectrum (Cl—CH$_4$) m/z=333 (M+1). NMR 300 MHz (CDCl$_3$) d 9.0 (s, 2H); 7.8 (d, 2H); 7.55 (s, 1H); 7.45 (d, 2H); 7.1 (s, 1H); 4.85 (s, 2H); 4.1 (s, 3H).

EXAMPLE 16

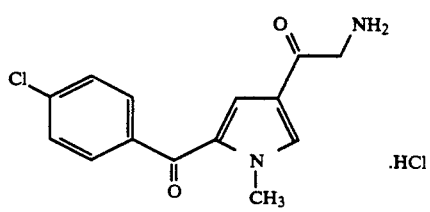

2-Amino-1-[5-(4-Chlorobenzoyl)-1-methyl-1H-pyrrol-3-yl]-ethanone hydrochloride (16)

6.18 g (0.0186 mole) 2-[(Bis-formyl)amino]-1-[5-(4-chlorobenzoyl)-1-methyl-1H-pyrrol-3-yl]-ethanone was stirred 3 days in 5% HCl/EtOH. A 0.5 mL portion of conc. HCL was added and the reaction stirred for two more days. The solid was collected by filtration. The solid was stirred in refluxing methanol and the undissolved solid collected by filtration and discarded. The filtrate was cooled to room temperature and diethyl ether was added. The solid was collected. It was twice treated with boiling methanol to give pure product: mp 290° C. (decomp.); mass spectrum (CH$_4$—Cl) m/z=277 (M+1); NMR (Me$_2$SO-d$_6$) d 8.2 (br s, 4H); 7.85 (d, 2H); 7.6 (d, 2H); 7.2 (s,1H); 4.3 (s, 2H); 4.0 (s 3H). Anal Calcd for C$_{14}$H$_{13}$ClN$_2$O$_2$.$_{HCl}$: C, 53.69; H, 4.51; N, 8.94. Found: C, 53.91; H, 4.4.1; N, 8.76.

What is claimed is:

1. A compound having anti-convulsant activity of the formula:

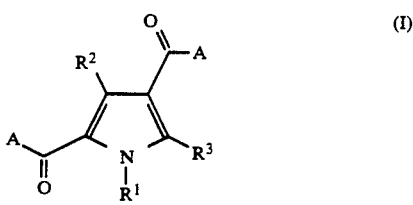

wherein,
A is simultaneously both

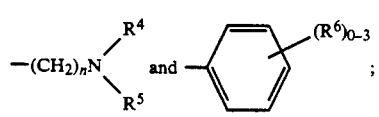

n is an integer from 1 to 5;
R$^1$ is selected from the group consisting of H and C$_{1-4}$alkyl;
R$^2$ and R$^3$ are selected from the group consisting of H and C$_{1-4}$alkyl;
R$^4$ and R$^5$ are independently selected from the group consisting of H, C$_{1-4}$alkyl, phenyl C$_{1-4}$alkyl and substituted phenyl $C_{1-4}$ alkyl where the substituent is on phenyl and selected from the group consisting of methyl and methoxy, or in the alternative, are fused and together with said nitrogen form a heterocyclic ring selected from the group consisting of:

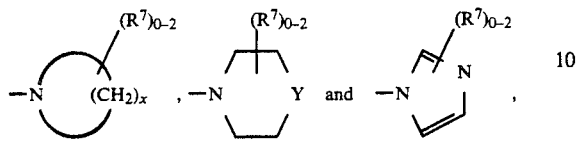

wherein Y is S or O, x is 3 to 7 and $R^7$ is selected from the group consisting of methyl and hydroxymethyl; and $R^6$ is selected from the group consisting of halo, $C_{1-4}$ alkyl, $C_{1-4}$alkoxy, hydroxy, nitro, amino, $C_{1-4}$acylamino, cyano, trihalo$C_{1-4}$alkyl, $C_{1-4}$alkylsulfonyl, $C_{1-4}$alkylsulfinyl, and $C_{1-4}$acyl, including pharmaceutically acceptable acid addition salts thereof.

2. The compound of claim 1 wherein $R^1$ is selected from the group consisting of hydrogen, methyl, ethyl, n-propyl and i-propyl.

3. The compound of claim 1 wherein $R^2$ and $R^3$ are independently selected from the group consisting of hydrogen, methyl, ethyl, n-propyl and i-propyl.

4. The compound of claim 1 wherein $R^4$ and $R^5$, where independently selected, are selected from the group consisting of hydrogen, methyl, ethyl, n-propyl, i-propyl, benzyl and phenylethyl where the phenyl ring may be mono- or di-substituted with a substituent selected from the group of methyl and methoxy.

5. The compound of claim 1 wherein $R^4$ and $R^5$, where fused and depicted together with nitrogen, are selected from the group consisting of:

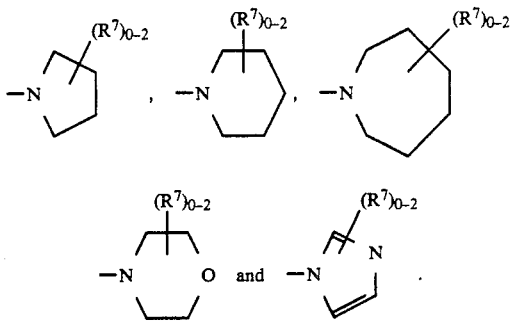

6. The compound of claim 1 wherein $R^6$ is selected from the group consisting of bromine, chlorine, methyl, ethyl, methoxy, ethoxy, hydroxy, nitro, amino, formylamino, acetylamino, cyano, perfluoromethyl, 3,3,3-trifluoropropyl, methylsulfonyl, methylsulfinyl, formyl, and acetyl.

7. The compound of claim 1 wherein said pharmaceutically acceptable salt is selected from the group consisting of hydrochlorides, sulfates, phosphates, methane sulfonates, fumarates, maleates, citrates and lactates.

8. The compound of claim 1 having the general formula:

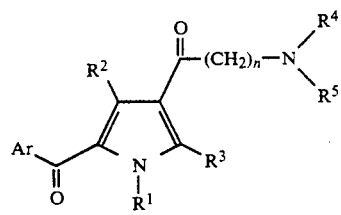

wherein Ar, $R^1$, $R^2$, $R^3$, $R^4$, $R^5$ and n are selected in concert from the group consisting of:

| n | $R^1$ | $R^2/R^3$ | $R^4/R^5$ | Ar |
|---|-------|-----------|-----------|-----|
| 1 | $CH_3$ | H/H | piperidinyl | p-ClPh |
| 1 | $CH_3$ | $CH_3/CH_3$ | morpholinyl | p-ClPh |
| 1 | $CH_3$ | $CH_3/CH_3$ | piperidinyl | p-ClPh |
| 1 | $CH_3$ | H/H | $CH_2CH_3/CH_2CH_3$ | p-ClPh |
| 1 | $CH_3$ | $CH_3/CH_3$ | pyrrolidinyl | p-ClPh |
| 1 | $CH_3$ | $CH_3/CH_3$ | imidazolyl | p-ClPh |

-continued

| n | R¹ | R²/R³ | R⁴/R⁵ | Ar |
|---|----|-------|-------|-----|
| 1 | CH₃ | CH₃/CH₃ | H / 3,4-dimethoxyphenethyl | p-ClPh |
| 1 | CH₃ | H/H | tetrahydropyran-2-yl | p-ClPh |
| 1 | CH₃ | CH₃/CH₃ | CH₃ / benzyl | p-ClPh |
| 1 | CH₃ | H/H | cyclohexyl | o-ClPh |
| 1 | CH₃ | H/H | cycloheptyl | p-ClPh |
| 1 | CH₃ | H/H | cyclopentyl | o-ClPh |
| 1 | CH₃ | H/H | 2,6-dimethyltetrahydropyran-4-yl | p-ClPh |
| 1 | CH₃ | H/H | 1-Adamantyl | o-ClPh |
| 1 | CH₃ | H/H | 2-(hydroxymethyl)cyclopentyl | p-ClPh |
| 1 | CH₃ | H/H | cyclooctyl | p-ClPh |
| 1 | CH₃ | H/H | 2H-pyrrol-2-yl | p-CH₃OPh |
| 1 | CH₃ | H/H | cyclohexyl | p-CH₃OPh |
| 1 | CH₃ | H/H | tetrahydropyran-2-yl | o-ClPh |

-continued
| n | R¹ | R²/R³ | R⁴/R⁵ | Ar |
|---|---|---|---|---|
| 1 | CH₃ | H/H |  | p-NO₂Ph |
| 1 | CH₃ | H/H |  | p-NO₂Ph |
| 1 | CH₃ | H/H | 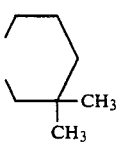 | p-ClPh |
| 1 | CH₃ | H/H |  | m-ClPh |
| 1 | CH₃ | H/H |  | m-ClPh |
| 1 | CH₃ | H/H |  | m-ClPh |
| 1 | H | H/H |  | p-ClPh |
| 1 | H | H/H |  | p-ClPh |
| 1 | CH₃ | H/H | H/CH₂CH₃ | p-ClPh |
| 1 | CH₃ | H/H | CH₂CH₃/CH₂CH₃ | p-CH₃OPh |
| 1 | CH₃ | H/H |  | p-ClPh |
| 1 | CH₃ | H/H |  | p-ClPh |
| 1 | CH₃ | CH₃/CH₃ | CH₂CH₃/CH₂CH₃ | p-ClPh |
| 1 | CH₃ | H/H |  | p-CH₃OPh |
| 1 | CH₃ | CH₃/CH₃ | CH₂CH₃/CH₂CH₃ | 2,4-diClPh |
| 1 | CH₃ | CH₃/CH₃ | CH₃/CH₃ | 2,4-diClPh |
| 1 | CH₃ | H/H | CH₃ 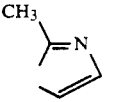 | p-ClPh |

| n | R¹ | R²/R³ | R⁴/R⁵ | Ar |
|---|----|-------|-------|-----|
| 4 | CH₃ | CH₃/CH₃ | CH₂CH₃/CH₂CH₃ | p-ClPh |
| 4 | CH₃ | CH₃/CH₃ |  | p-ClPh |
| 1 | CH₃ | CH₃/CH₃ |  | 2,4-diClPh |
| 3 | CH₃ | H/H |  | p-pyroolidin-1-yl-Ph |
| and 1 | CH₃ | H/H | H/H | p-ClPh. |

9. The compound of claim 1 selected from the group consisting of:

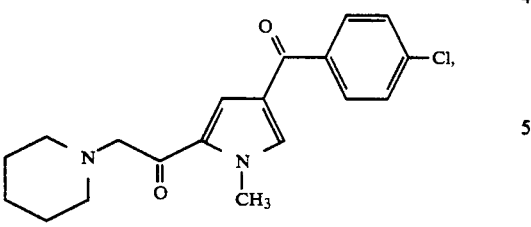

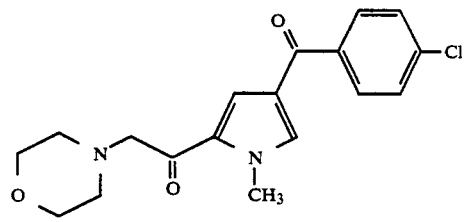

and

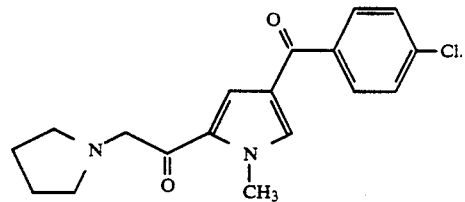

10. A pharmaceutical composition effective as an anticonvulsant in mammals comprising an effective amount of active compound of claim 1 and a pharmaceutically acceptable carrier.

11. A method for treating seizures in mammals comprising administering an effective amount of an active compound of claim 1 in a pharmaceutically acceptable carrier.

* * * * *